United States Patent [19]
Dittrich et al.

[11] Patent Number: 5,776,063
[45] Date of Patent: Jul. 7, 1998

[54] ANALYSIS OF ULTRASOUND IMAGES IN THE PRESENCE OF CONTRAST AGENT

[75] Inventors: Howard Dittrich; Harold Levene, both of San Diego; Eric Mjolsness, Encinitas, all of Calif.

[73] Assignee: Molecular Biosystems, Inc., San Diego, Calif.

[21] Appl. No.: 723,898

[22] Filed: Sep. 30, 1996

[51] Int. Cl.$^6$ .............................. A61B 5/00; A61B 8/00
[52] U.S. Cl. .............................. 600/408; 600/458
[58] Field of Search .................. 128/662.02, 660.04, 128/660.05, 660.06, 600.07; 382/128–132, 155–160, 165, 180, 195, 224–228; 395/21–22, 50; 424/9.1, 9.3, 9.4, 9.5, 9.51, 9.52, 9.6, 9.61; 600/458, 440, 441, 442, 443

[56] References Cited

U.S. PATENT DOCUMENTS

| | | | |
|---|---|---|---|
| 5,260,871 | 11/1993 | Goldberg | 364/413.02 |
| 5,417,215 | 5/1995 | Evans et al. | 128/660.06 |
| 5,425,366 | 6/1995 | Reinhardt et al. | 128/662.02 |
| 5,577,505 | 11/1996 | Brock-Fisher | 128/662.02 |

OTHER PUBLICATIONS

Cios, et al., *Use of Neural Networks in Detecting Cardiac Diseases from Echocardiographic Images*, IEEE Engineering in Medicine and Biology, pp. 58–60, Sep. 1990.

DaPonte and Sherman, *Classification of Ultrasonic Image Texture by Statistical Discriminant Analysis and Neural Networks*, Computerized Medical Imaging and Graphics 15(1):3, Jan.–Feb. 1991.

Watabe and Mizoshiri, *Discrimination of Normal and Infarcted Myocardium and Consideration of the Textural Distinction Using Neural Network*, Faculty of Science and Engineering, Ritsumeikan University, Kyoto–shi 803, pp. 1–14 (Japanese copy and translation provided).

Marple, et al., *Application of Time–Frequency and Time–Scale Analysis to Underwater Acoustic Transients*, Presented at 26th Asilomar, Conference on Signals, Systems & Computers, Oct. 1992.

Brotherton and Mears, *Application of Neural Nets to Feature Fusion*, Presented at 26th Asilomar, Conference on Signals, Systems & Computers, Oct. 1992.

Fujita, et al., *Neural network approach for the computer–aided diagnosis of coronary artery diseases in myocardial SPECT bull's eye images*, Radiologia diagnostica, 35(1):15, 1994.

(List continued on next page.)

*Primary Examiner*—Frances Jaworski
*Attorney, Agent, or Firm*—Fish & Richardson P.C.

[57] ABSTRACT

A method and apparatus for directly identifying and characterizing input data derived from regions of interest in ultrasound images of organs in the presence of attenuation from interposed contrast agent, for the purpose of diagnosing abnormalities. The input data is classified into one of a number of classes depending upon the characteristics of that data, in order to distinguish normal conditions from abnormal conditions. The invention is based on the recognition that significant information relating to the health of tissue exists in regions of interest in ultrasound images in the presence of attenuation from interposed contrast agent. This information is in the form of backscatter speckle patterns that have "texture" characteristics that are distinguishable in healthy versus diseased tissue. The invention classifies such patterns as probably normal or abnormal by means of an analysis system that may include a neural network system. The preferred embodiment of the present invention includes: (1) a data acquisition system for acquiring ultrasound image data indicative of a region of interest in the presence of attenuation from interposed contrast agent; (2) an optional signal conditioning stage to remove signals (e.g., noise) from the input data; and (3) an analysis system designed to detect "texture" characteristics that distinguish healthy tissue from diseased tissue even in the presence of the contrast agent. The output classifies the input data in a uniform, unambiguous manner. The invention is preferably implemented as a computer program executing on a programmable computer.

66 Claims, 16 Drawing Sheets

OTHER PUBLICATIONS

Yi. et al., *Study of Echocardiogram for Myocardial Infarction Using Neural Networks*, Proceedings of the Annual International Conference of the IEEE Engineering in Medicine and Biology Society, 15:255, Oct. 28–31, 1993.

Yi. et al. *A New Neural Network Algorithm to Study Myocardial Reflected Ultrasound for Tissue Characterization*, IEEE Bioengineering Proceedings of the Northeast Conference, pp. 109–110, 1993.

Wang and Karvelis, *Computer interpretation of thallium SPECT studies based on neural network analysis*, SPIE 1445:574, 1991.

Gail A. Carpenter, *Neural Network Models for Pattern Recognition and Associative Memory*, Neural Networks 2:243, 1989.

Fisher, et al., *Neural Networks in Ventilation–Perfusion Imaging; Part I. Effects of Interpretive Criteria and Network Architecture*, Radiology, 198(3):699, Mar. 1996.

Abe, et al., *Computer–Aided Detection of Diffuse Liver Disease in Ultrasound Images*, Investigative Radiology 27:71, Jan. 1992.

Hansen and Salamon, *Neural Network Ensembles*, IEEE Transactions of Pattern Analysis and Machine Intelligence, 12(10):993, Oct. 1990.

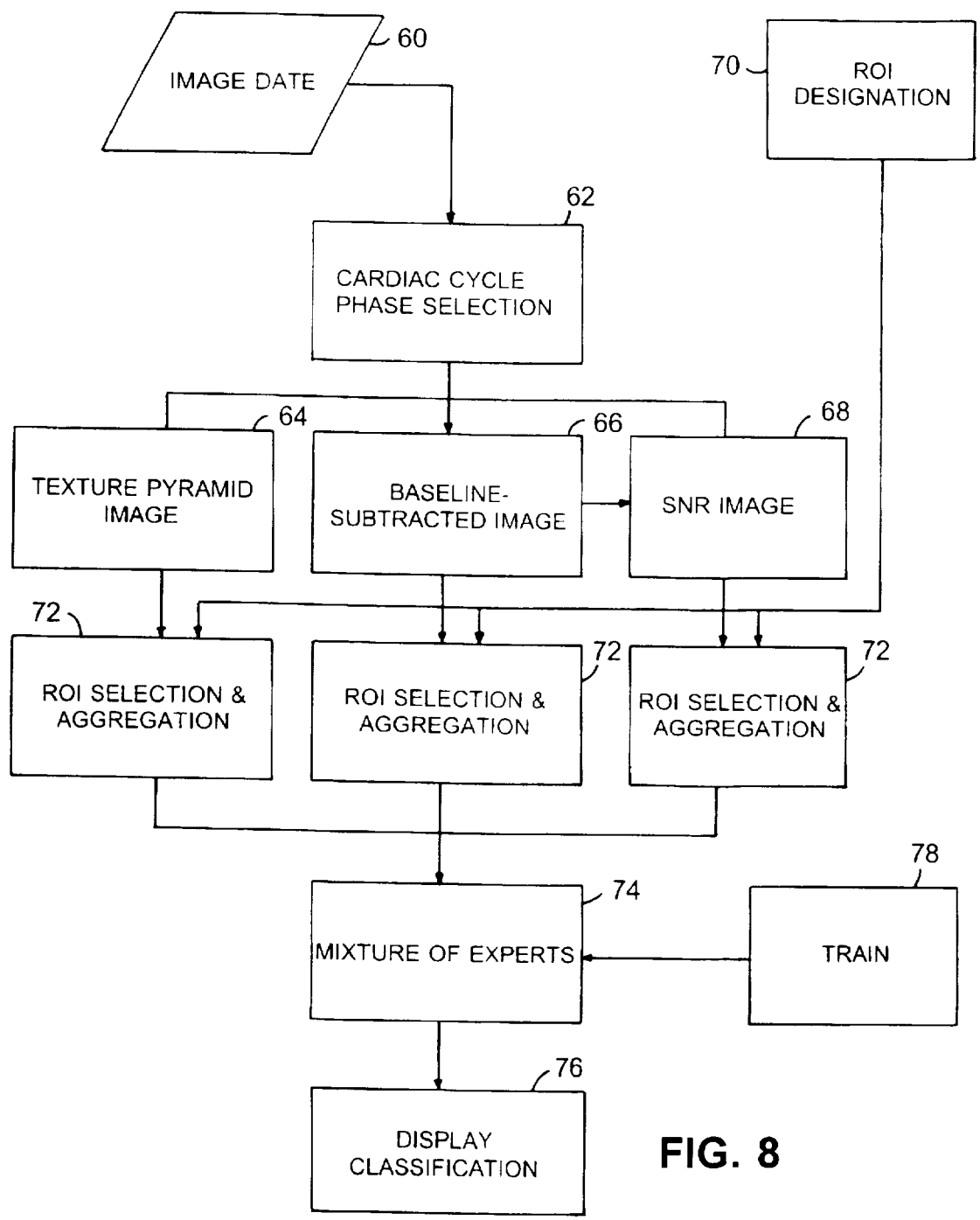

INPUT LAYER    HIDDEN LAYER    OUTPUT LAYER 5,776,063

1

ANALYSIS OF ULTRASOUND IMAGES IN THE PRESENCE OF CONTRAST AGENT

BACKGROUND OF THE INVENTION

1. Field of the Invention

This invention relates to a method and apparatus for analysis of ultrasound images of organs in the presence of contrast agent.

2. Description of Related Art

In the medical arts, there is a continuing need to determine the nature of internal anatomical or other in vivo structures and physiological processes of patients for purposes of diagnosis, therapy, and prognosis. Analysis, detection, and classification of both steady-state signals representative of anatomical and other in vivo structures and transient signals representative of ongoing processes are important in a number of medical applications.

One such application is the detection of cardiac abnormalities. Heart disease is one of the leading causes of death in the Western world, including the United States. Heart disease is often due to coronary artery disease, resulting in myocardial infarction. If cardiac disease could be identified before a cardiac event occurs, appropriate treatment might prevent some complications of heart disease.

A wide variety of methods are presently available for generating data representation of the nature of anatomical and other in vivo structures and physiological processes, which make diagnosing and/or therapy easier. For example, angiography is presently used to identify and quantify occlusion and stenosis in the coronary artery. In recent years, a form of ultrasound known as echocardiography has also been used extensively as a diagnostic tool for identifying cardiac problems. The use of echocardiography as a diagnostic tool has the advantages of being non-invasive and relatively accurate in portraying anatomical structures.

Echocardiography provides large amounts of numeric or image data. The data must then be interpreted in order to classify the information. For example, an ultrasound image typically is read by a skilled technician or physician to determine whether the signs of heart disease are present in a patient, and the extent of those signs. If the patient is classified as having heart disease, knowledge of the extent of disease allows for appropriate therapy and prognostic classification.

Presently, in many applications data is presented in a visual format which requires a highly skilled technologist to detect significant "signature" characteristics in the data which in turn reveal traits of an anatomical or other in vivo structure or physiological process. Such data is commonly displayed on a printed chart, photographic film, or video display monitor, such as a cathode ray tube (CRT) or liquid crystal display (LCD). However, data from any particular system is often difficult to interpret because of limitations of the data collection system and the presence of unwanted signals ("noise").

In particular, in ultrasound systems, interpretation of data can be particularly difficult. In order to improve image quality, image enhancement agents, or "contrast" agents, have been developed. A contrast agent is designed to backscatter ultrasound energy, and is administered to a patient as an ultrasound image is taken. Typical contrast agents comprise tiny "bubbles" filled with a fluid (liquid or gas) having desired sound reflective properties. However, ultrasound contrast agents include, but are not limited to, liquid emulsions, solids, encapsulated fluids, encapsulated bio-compatible gases and combinations thereof. Fluorinated liquids and gases are especially useful in contrast compositions. The gaseous agents are of particular importance because of their efficiency as a reflector of ultrasound. Resonant gas bubbles scatter sound a thousand times more efficiently than a solid particle of the same size. These types of agents include free bubbles of gas as well as those which are encapsulated by a shell material. A contrast agent may be administered via any of the known routes, including, but are not limited to, intravenous (IV), intramuscular (IM), intraarterial (IA), and intracardiac (IC).

A contrast agent typically perfuses in surrounding tissue at different rates depending on the health and nature of the tissue (generally, healthy tissue has more capillaries than damaged tissue, and thus contrast agent perfuses more readily through healthy tissue). Backscattered ultrasound energy from the different levels of contrast agent in tissue results in a differentiated image. By analyzing one or more ultrasound images, a skilled technologist can determine a diagnosis.

Even with contrast agents, ultrasound images are particularly difficult to interpret because of uneven attenuation. "Attenuation" is a measure of the scattering, reflection, and absorption of ultrasonic energy by a particular substance whereby less of the energy passes entirely through that substance and beyond. For example, such variations in attenuation in different materials is the basis for echocardiography. However, if the ultrasound energy is significantly attenuated during transmission through a substance, the backscattering signal posterior to that substance with respect to the ultrasound transducer will be diminished, thereby causing the posterior region to appear dark, regardless of the backscatter coefficient of material in that region. This is termed "shadowing." The shadowing effect causes portions of an ultrasound image to appear dark when, in fact, contrast agent is actually present in the tissue. Significant attenuation does not allow for true visualization of the contrast agent which appears in the tissue/organs beyond the attenuating areas, and can lead to a false diagnosis.

An example of the attenuation effect on the posterior myocardial wall in an echocardiographic image of a heart 10 is shown in FIGS. 1A and 1B. FIG. 1A is an echocardiographic image of the heart 10 before contrast agent is introduced. FIG. 1B is an echocardiographic image of the heart 10 after contrast agent is introduced. An ultrasound transducer 20 is located at the apex of the sector. The heart muscle 10 comprises three regions of interest (ROI): anterior region 12 (i.e., closest to the transducer 20 and in front of the heart chamber 18), lateral region 14, and posterior region 16 (i.e., furthest away from transducer 20). The heart chamber 18 is positioned between the posterior region 16 and the transducer 20. Before introduction of a contrast agent, the entire myocardium is visible, as shown in FIG. 1A.

However, with the introduction of a contrast agent into the heart chamber 18 in FIG. 1B, the contrast agent absorbs and reflects much of the ultrasound energy, preventing it from reaching the posterior region 16. The posterior region 16 appears dark in images, even though it may actually be experiencing some degree of perfusion with the contrast agent. The anterior region 12 is not significantly affected. The lateral regions 14 are affected to an intermediate degree, since some shadowing results from the anterior region 12. Accordingly, it has been considered that no useful information can be derived from the posterior, or "far field", region of interest (ROI) when an echocardiographic image is taken in the presence of a contrast agent, and only impaired or "noisy" information can be derived from the lateral regions 14 until the contrast agent clears sufficiently from the organ.

From the detected wave reflections, graphs may be generated, such as shown in FIGS. 2A–2C. These graphs represent the mean image intensity of a particular ROI as a function of time in the presence of a contrast agent.

FIG. 2A is a conventional time-intensity curve for heart anterior region 12, with a sonification frequency of approximately 30 frames per second (fps). The curve represents frames selected from a single point in the cardiac cycle. From time at zero (i.e., the extreme left-hand side of the graph) to a maximum 24, the increasing portion of this graph is due to the wash-in of contrast agent into the anterior region 12. At the maximum 24, the anterior region 12 reaches its greatest concentration of contrast agent. From the maximum 24 until time at infinity, the gradual decreasing intensity is conventionally ascribed to wash-out of contrast agent (i.e., decreasing concentration of contrast agent as the heart pumps through blood not imbued with contrast agent) from the anterior region 12. Under this conventional interpretation, the time-intensity curve for this region of interest indicates that the anterior region 12 is normal, healthy tissue.

FIG. 2B depicts the lateral region 14 of the heart 10 that might be characterized by a disease condition, such as ischemia, where the blood circulation to tissue in the lateral region 14 is less than optimal. Because the blood flow is not optimal, it can be seen that the maximum 27 is lower than the maximum 24 in the anterior region 12 and that the time to reach the maximum in the lateral region 14 is greater than the time to reach the maximum in the anterior region 12. The lateral region 14, known to be only somewhat affected by attenuation, shows a delay in both the time and intensity of the contrast agent. The conventional interpretation of this graph indicates an abnormality in that ROI.

The time-intensity graph in FIG. 2C exhibits the effects of significant shadowing resulting from attenuation. Assuming that posterior region 16 is as healthy as the anterior region 12, the "actual" profiles of intensity should look approximately the same if attenuation effects did not exist. Thus, if the posterior region 16 were anterior (as opposed to posterior) to the transducer 20, the dotted profile 25 would appear as the time intensity curve. However, in actuality, as the heart chamber 18 fills with contrast agent prior to perfusion in the posterior region 16, the contrast agent in the chamber 18 attenuates most of the ultrasound energy that might have penetrated and scattered off of the posterior region 16. Thus, as seen in FIG. 2C, the intensity of the posterior region 16 drops off to almost zero regardless of whether perfusion occurs in that region.

At some time after the heart chamber 18 reaches its maximum concentration of contrast agent, the effects of attenuation begin to wear off and the echo intensity in the posterior region 16 begins to increase. However, a trained diagnostician would note that the maximum intensity in the posterior region 16 is lower than for the anterior region 12 and occurs later in time. This response is similar to the response given for the diseased lateral region 14. Thus, the potential to falsely diagnose the posterior region 16 as diseased exists when in fact the problem may be due entirely to the effects of attenuation.

Moreover, it has recently been discovered that the sonification frequency (the frequency at which ultrasound images are generated) affects simple time-intensity plots such as are shown in FIGS. 2A–2C. For example, FIG. 2D shows the same regions as FIG. 2A, but with a sonification frequency of about one frame per second (fps). The decay rate of the curve 28 in FIG. 2D is far less than the decay rate shown in FIG. 2A. It is now believed that the ultrasound beam contains sufficient energy to destroy or alter contrast agent "bubbles" during imaging. Thus, the higher the frequency of imaging, the more bubbles destroyed or altered, resulting in loss of intensity of the reflected sound. Accordingly, such simple time-intensity curves for diagnosing disease conditions are lacking as accurate diagnostic tools.

Other diagnostic tools, such as histograms of pixel intensity of ultrasound images, have been used in an attempt to detect disease in tissue. However, a histogram which displays the range of pixel intensity within a region of interest may change without a net increase in overall intensity. The distribution of intensity within a region of interest, during passage of contrast agent through the tissue, may change from a few bright and many dim pixels to a greater proportion of medium intensity pixels. Such a change is shown in FIGS. 2E and 2F. FIG. 2E is a histogram of a region of interest in a pre-contrast echocardiographic image showing a small number of bright pixels and a large number of dim pixels, and having an overall mean intensity of about 77.47. FIG. 2F is a histogram of a region of interest in a peak contrast echocardiographic image showing a mostly medium intensity pixels, having an overall average intensity of 77.60, approximately equal to the overall average intensity of FIG. 2E. The histograms visually indicate that differences exist in the two images, but generating conventional statistics can mask such differences. Accordingly, this method may fail to reliably distinguish healthy from diseased tissue in ultrasound images of organs in the presence of contrast agent, especially in mid (e.g., lateral) and far field images.

Thus, there is a need for a method and apparatus for accurately and consistently analyzing far field regions of ultrasound images of organs in the presence of attenuation from interposed contrast agent. The present invention provides such a method and apparatus.

SUMMARY OF THE INVENTION

The invention is a method and apparatus for characterizing data in regions of interest of ultrasound images of organs, particularly echocardiographic images, in the presence of attenuation from interposed contrast agent, for the purpose of diagnosing abnormalities, such as ischemia. The invention includes a method and apparatus for detecting and analyzing such abnormalities by means of an analysis system that preferably includes a neural network system.

In developing the present invention, it was recognized that significant information relating to the health of tissue in fact exists in mid field and far field regions of interest in ultrasound images in the presence of attenuation from interposed contrast agent. This information is in the form of backscatter speckle patterns that have "texture" characteristics that are distinguishable in healthy versus diseased tissue. However, such patterns are difficult to discern and classify manually or by using simple statistical or time-intensity analysis. Accordingly, the invention applies neural network and other analysis techniques to analyze such speckle patterns. The invention is preferably applied to a time sequence of images.

The invention can be used to analyze ultrasound images of any organ under similar conditions. That is, any tissue or organ that receives a flow of blood may have images processed in the manner of the invention. These tissues/organs may include, but are not limited to, the kidneys, liver, brain, testes, muscles, and heart.

The invention can be used with any of several ultrasound imaging modalities, including conventional B-mode or gray scale ultrasound, Doppler ultrasound, 3D ultrasound, and harmonic ultrasound imaging. The invention may be used with high frequency (e.g., more than about 10 fps) and low frequency (e.g., less than or equal to about 10 fps) sonification rates. The invention may also be used with images taken from any orientation (e.g., short axis or long axis) or location.

The preferred embodiment of the present invention includes: (1) a data acquisition system for acquiring ultrasound image data indicative of a region of interest in the presence of attenuation from interposed contrast agent; (2) an optional signal conditioning stage to remove signals (e.g., noise) from the input data; and (3) an analysis system designed to detect "texture" characteristics that distinguish healthy tissue from diseased tissue even in the presence of the contrast agent. In the preferred embodiment, the analysis system includes a neural network trained using a back-propagation algorithm. The output classifies the input data in a uniform, unambiguous manner. The invention is preferably implemented as a computer program executing on a programmable computer.

The present invention provides a method by which attenuated ultrasound data can be directly classified without the need to display a complex and enigmatic image or other confusing output format which must be interpreted by a highly skilled technician.

It should be understood that the present invention is not limited in scope to this narrow embodiment. For example, the present invention can be applied to characterizing two-dimensional image data derived from X-rays, MRI devices, CT, PET, SPECT, and other image-generating techniques where regions of interest distinguishable by comparable "texture" characteristics are at least briefly obscured or shadowed by the presence of a contrast agent suited to each imaging modality.

BRIEF DESCRIPTION OF THE DRAWINGS

FIG. 8 is a more detailed block diagram of an embodiment of the analysis system used in the present invention to analyze regions of interest in ultrasound images in the presence of attenuation from interposed contrast agent, for the purpose of diagnosing abnormalities.

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Overview

The present invention is an analysis method and apparatus for directly identifying and characterizing input data derived from regions of interest in ultrasound images of organs in the presence of attenuation from interposed contrast agent, for the purpose of diagnosing abnormalities. The input data is classified into one of a number of classes depending upon the characteristics of that data, in order to distinguish normal conditions from abnormal conditions.

In developing the present invention, it was recognized that significant information relating to the health of tissue in fact exists in regions of interest in ultrasound images in the presence of attenuation from interposed contrast agent. This information is in the form of backscatter speckle patterns that have "texture" characteristics that are distinguishable in healthy versus diseased tissue. However, such patterns are difficult to discern and classify manually. Accordingly, the invention applies specialized analysis techniques, including neural network techniques, to analyze such texture patterns.

More particularly, the invention is based in part on the observation that intravenous injection of ultrasound contrast agent into an organ results in a visual change in the texture of tissue as perfusion takes place. This change is identifiable visually even when contrast agent is present between the transducer and the region of interest. It is this visually apparent change in texture which can be identified and "learned" by an analysis system such as a neural network. It is anticipated that an appropriate analysis system will be able to distinguish normally perfused, non-perfused, and highly (hyperemic) perfused segments of an organ. In addition, there is convincing preliminary data from animal studies that the contrast agent effect in tissue supplied by a moderate arterial stenosis is diminished and a visual change in texture from baseline or non-perfused tissue can be detected.

Figure 1A:
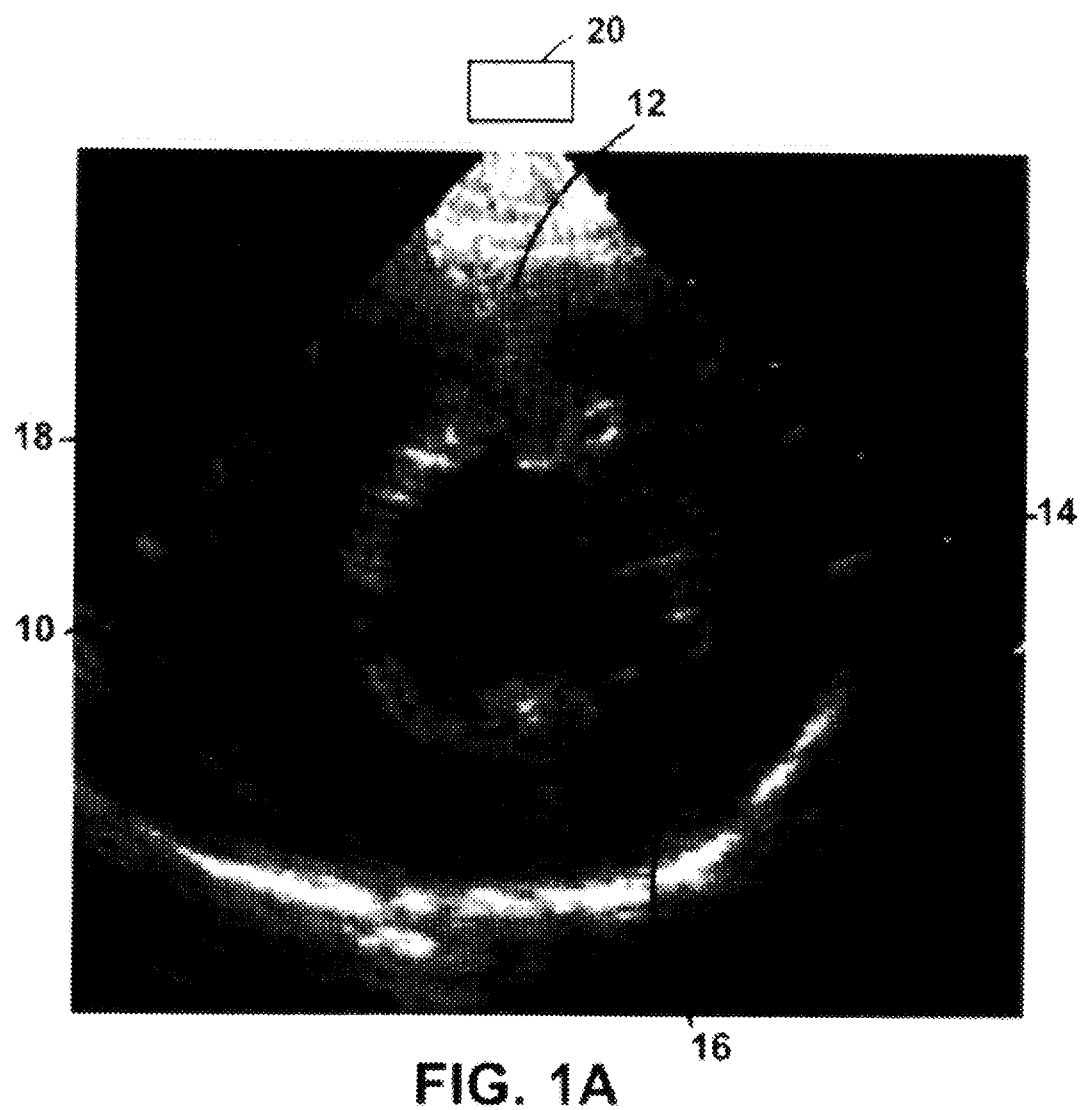
FIG. 1A is a prior art echocardiographic image of a heart before contrast agent is introduced.
Figure 1B:
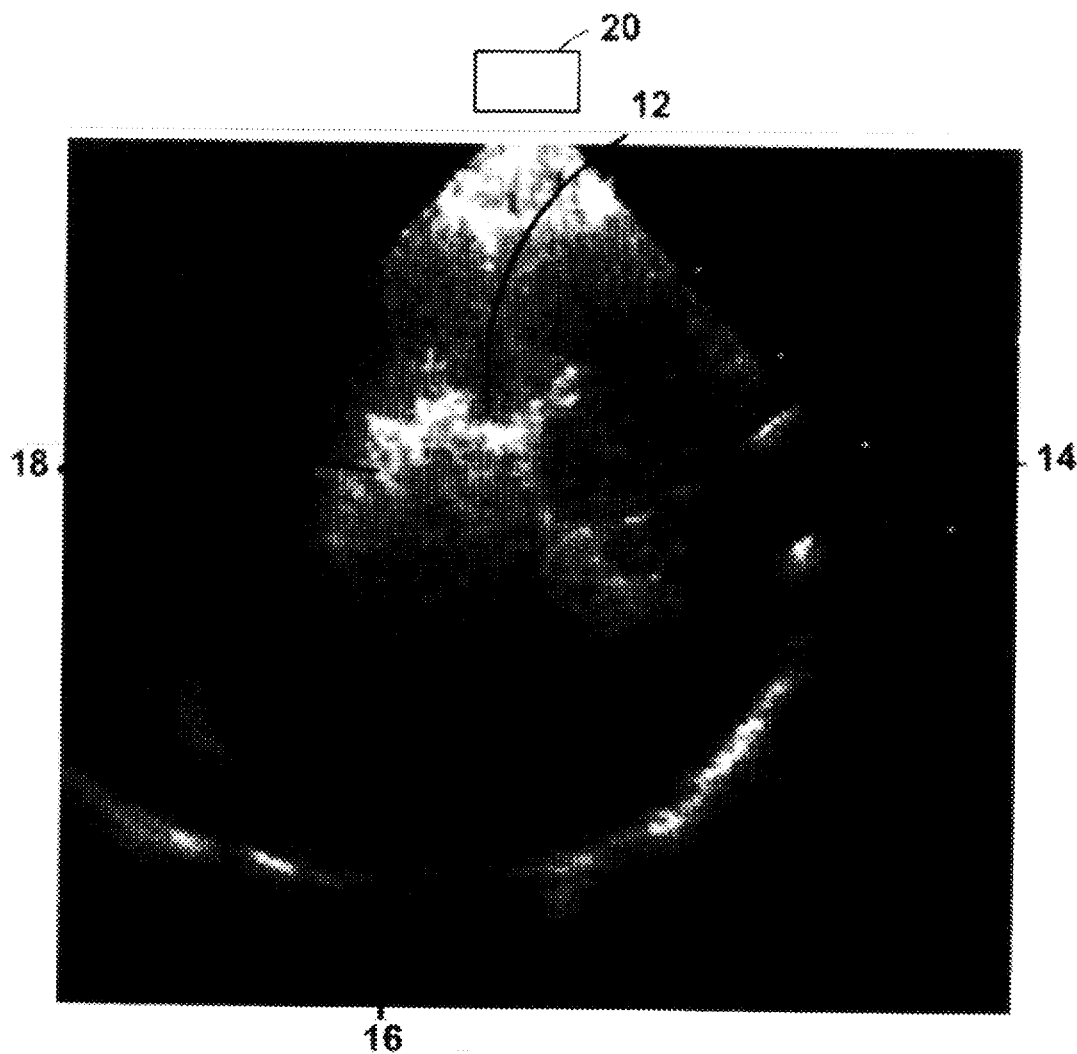
FIG. 1B is a prior art echocardiographic image of a heart after contrast agent is introduced.
Figure 2A:
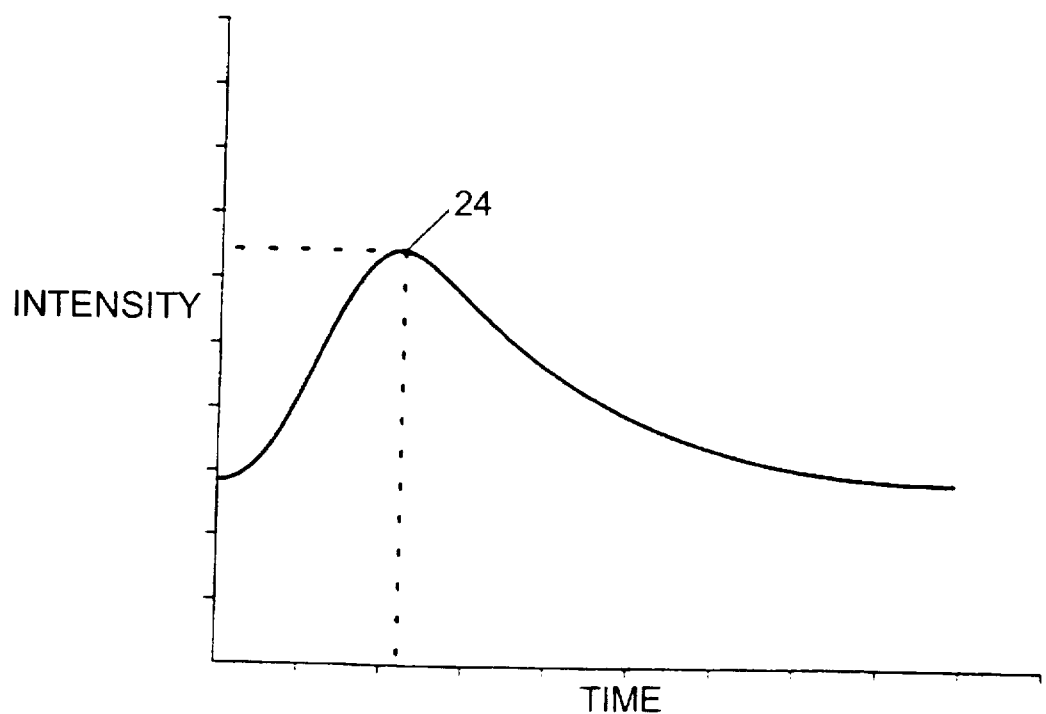
FIG. 2A is a graph of the mean image intensity of a prior art echocardiographic image of the anterior region of the heart as a function of time in the presence of a contrast agent, using a sonification frequency of about 30 fps.
Figure 2B:
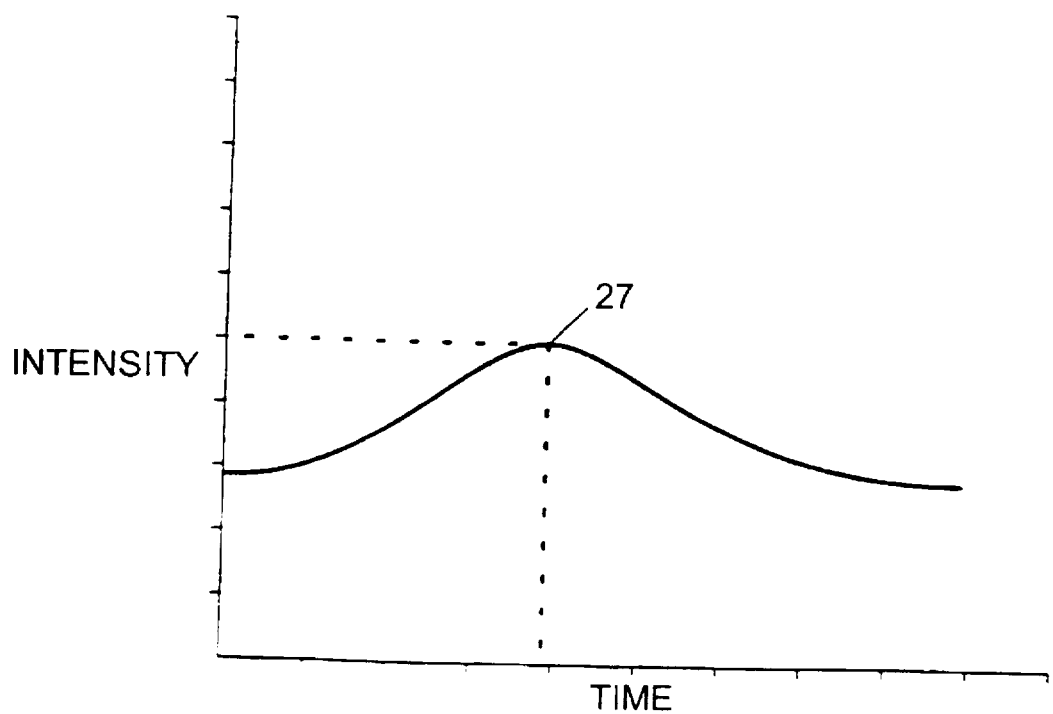
FIG. 2B is a graph of the mean image intensity of a prior art echocardiographic image of a lateral region of the heart as a function of time in the presence of a contrast agent, using a sonification frequency of about 30 fps.
Figure 2C:
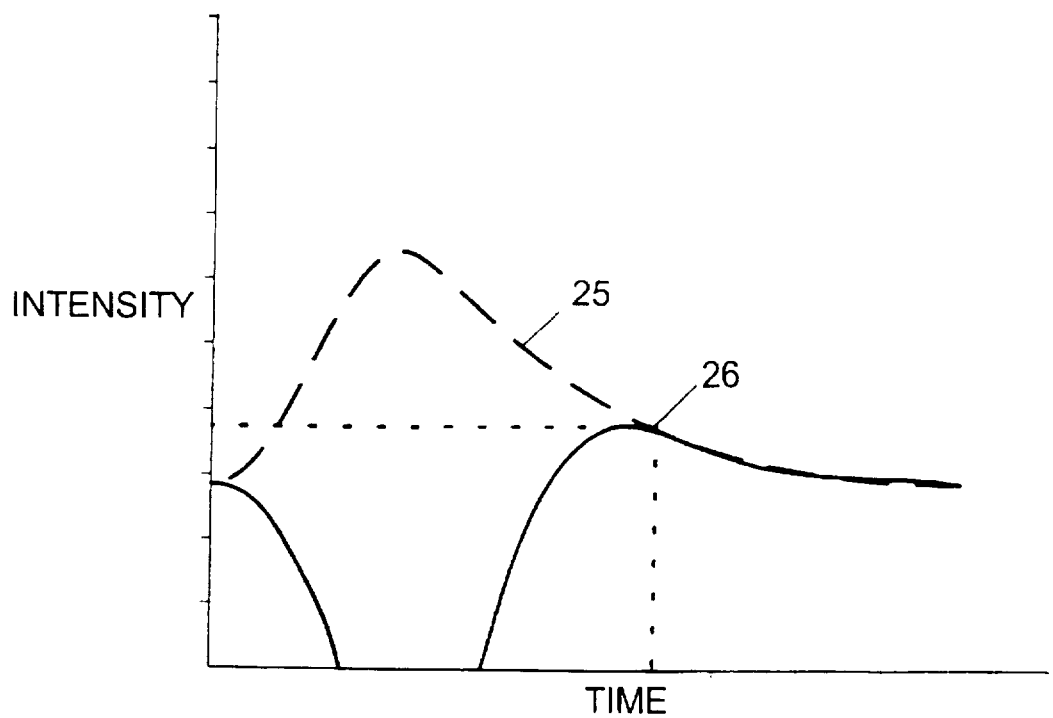
FIG. 2C is a graph of the mean image intensity of a prior art echocardiographic image of the posterior region of the heart as a function of time in the presence of a contrast agent, using a sonification frequency of about 30 fps.
Figure 2D:
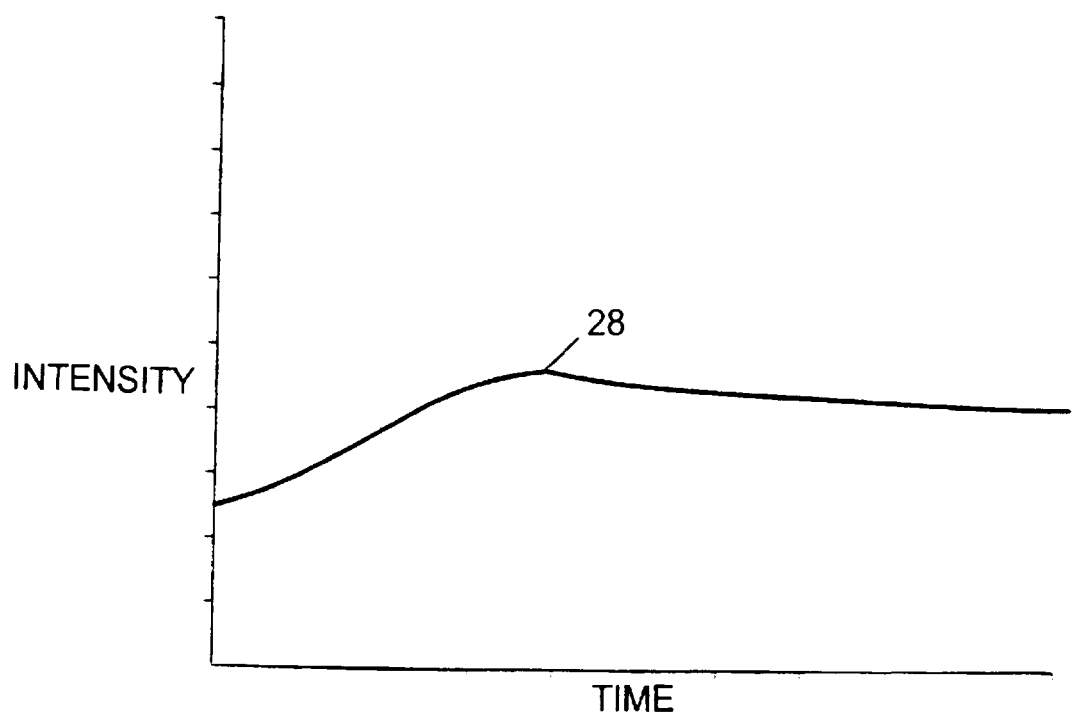
FIG. 2D is a graph of the mean image intensity of a prior art echocardiographic image of the anterior region of the heart as a function of time in the presence of a contrast agent, using a sonification frequency of about one fps.
Figure 2E:
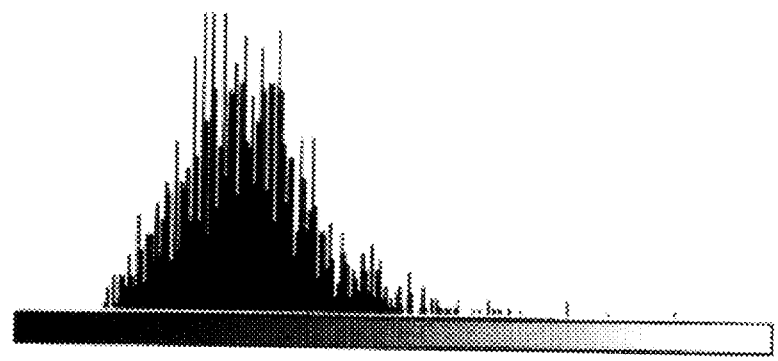
FIG. 2E is a histogram of a region of interest in a pre-contrast prior art echocardiographic image showing a small number of bright pixels and a large number of dim and intermediate brightness pixels, and having an overall average intensity.
Figure 2F:
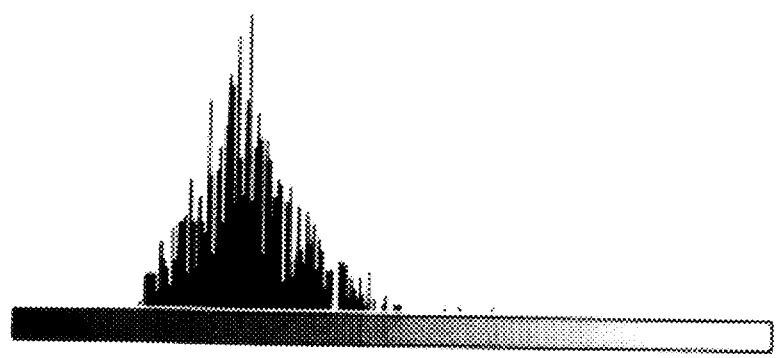
FIG. 2F is a histogram of a region of interest in a peak contrast prior art echocardiographic image showing mostly medium intensity pixels, having an overall average intensity approximately equal to the overall average intensity of FIG. 2E.

As noted above, time-intensity curves and means of histograms generally do not reflect this texture change. Mean pixel intensity may in fact decrease, as the examples in FIGS. 2C, 2E, and 2F demonstrate, at a time when a perceptible contrast effect exists in the tissue.

Figure 3A:
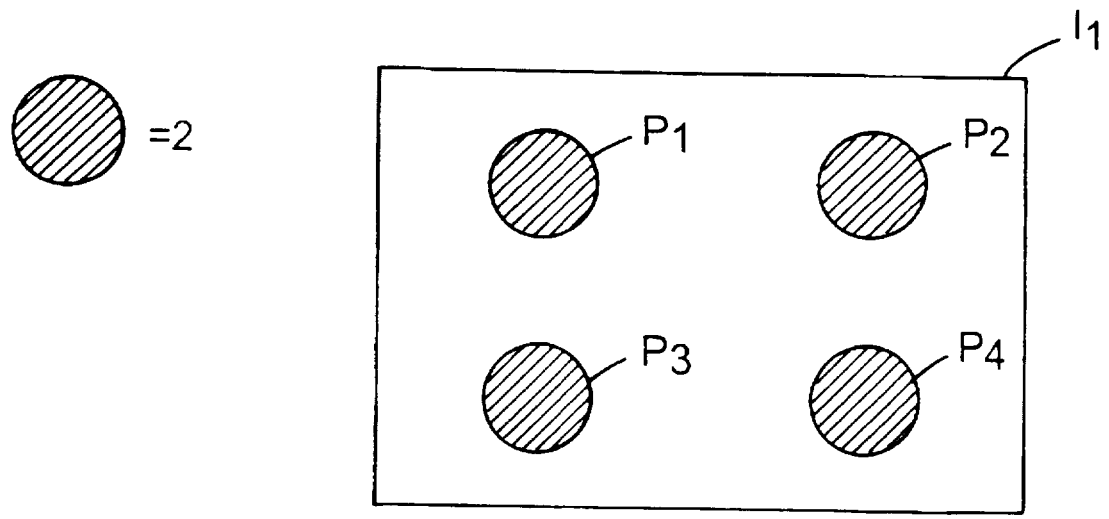
FIGS. 3A and 3B are stylized drawings showing conceptually how textural changes can occur yet be glossed over by prior art analysis techniques.
Figure 3B:
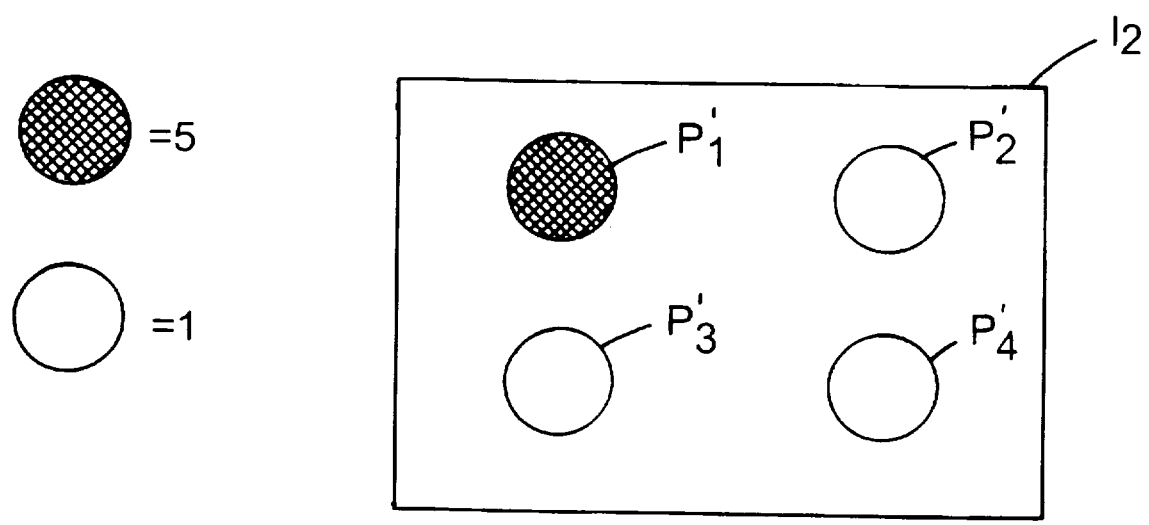

FIGS. 3A and 3B are stylized drawings showing conceptually how such textural changes can occur yet be glossed over by prior art analysis techniques. In FIG. 3A, a region of interest $I_1$ has 4 pixels $P_1$, $P_2$, $P_3$, $P_4$, each having the same intensity (e.g., 2). The average intensity over the region of interest is thus 2. The visual appearance of region of interest $I_1$ will be quite uniform.

In FIG. 3B, a region of interest $I_2$ has 4 pixels $P_1'$, $P_2'$, $P_3'$, $P_4'$. Pixels $P_2'$, $P_3'$, $P_4'$ each have the same lower intensity (e.g., 1), while pixel $P_1'$ has a much higher intensity (e.g., 5). The average intensity over the region of interest is thus still 2. However, the visual appearance of region of interest $I_2$ will not be as uniform as the visual appearance of region of interest $I_1$. Thus, a neural network can be trained to distinguish the two regions of interest.

Preferred Apparatus

The invention will be described in the context of conventional B-mode ultrasound as presently used in echocardiography. However, it should be understood that the invention can be used to analyze ultrasound images of other organs under similar conditions. The invention can be used with any of several other ultrasound imaging modalities, including Doppler ultrasound, three-dimensional ultrasound, and harmonic ultrasound imaging. The invention may be used with high frequency (e.g., more than about 10 fps) and low frequency (e.g., less than or equal to about 10 fps) sonification rates. The invention may also be used with images taken from any orientation (e.g., short axis or long axis) or location (e.g., parasternal or apical).

Figure 4:
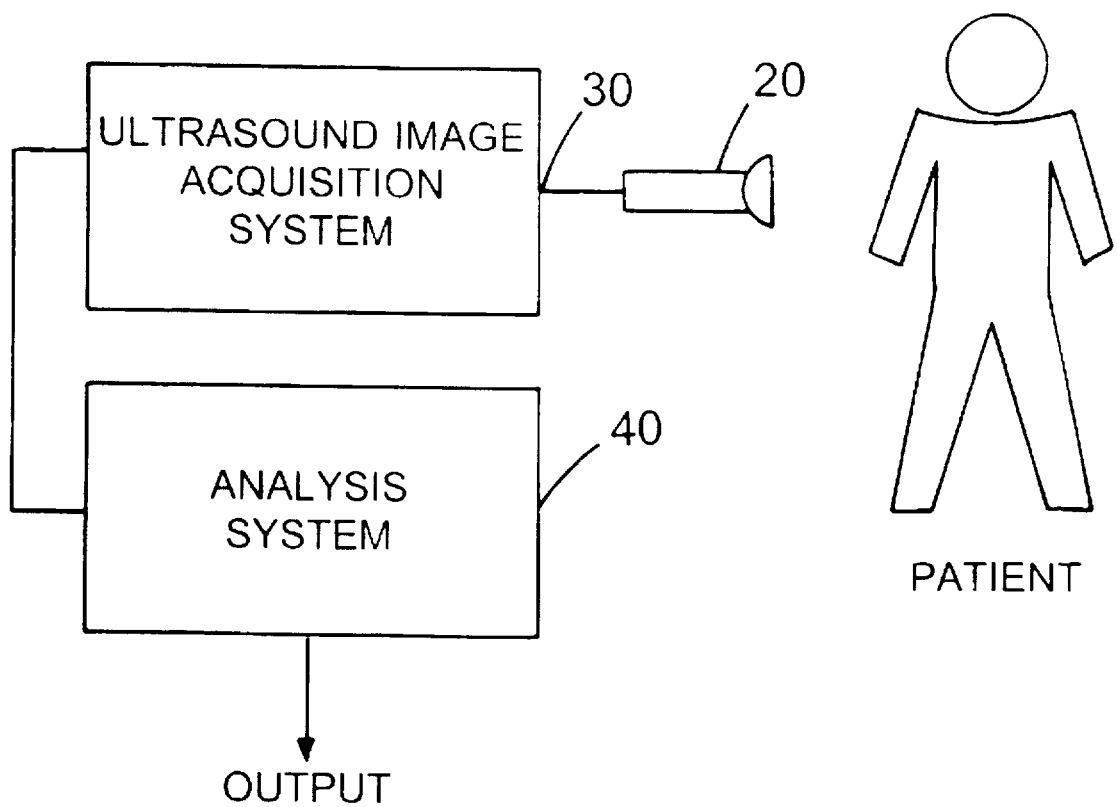
FIG. 4 is a block diagram of a simplified embodiment of the present invention used to generate and analyze regions of interest in ultrasound images in the presence of attenuation from interposed contrast agent, for the purpose of diagnosing abnormalities.

FIG. 4 is a block diagram of a simplified embodiment of the present invention used to generate and analyze regions of interest in ultrasound images in the presence of attenuation from interposed contrast agent, for the purpose of diagnosing abnormalities. A transducer 20 is coupled to a conventional echocardiographic image acquisition system 30. In the preferred embodiment, the output of the transducer 20 is gated so that images of the heart of a patient 35 are captured at corresponding points in time during the cardiac cycle. Electrocardiographic (ECG) data can be used to perform such gating, in known fashion.

The echocardiographic image acquisition system 30 may provide analog images that are captured to video tape and later digitized, or provide a direct digital output. In any event, in the preferred embodiment, the echocardiographic image acquisition system 30 preferably provides a time series of digital images of selected regions of the heart of the patient 35 as output for further analysis. The time sequence of images includes images of myocardial tissue before, during, and after administration of a contrast agent.

The output of the echocardiographic image acquisition system 30 is coupled to an analysis system 40, which is configured and operated as described below. The output of the analysis system 40 can be printed or displayed in any desired fashion, and can be a simple indication of probable diagnosis or as elaborate a textual and/or graphical report as desired.

Figure 5:
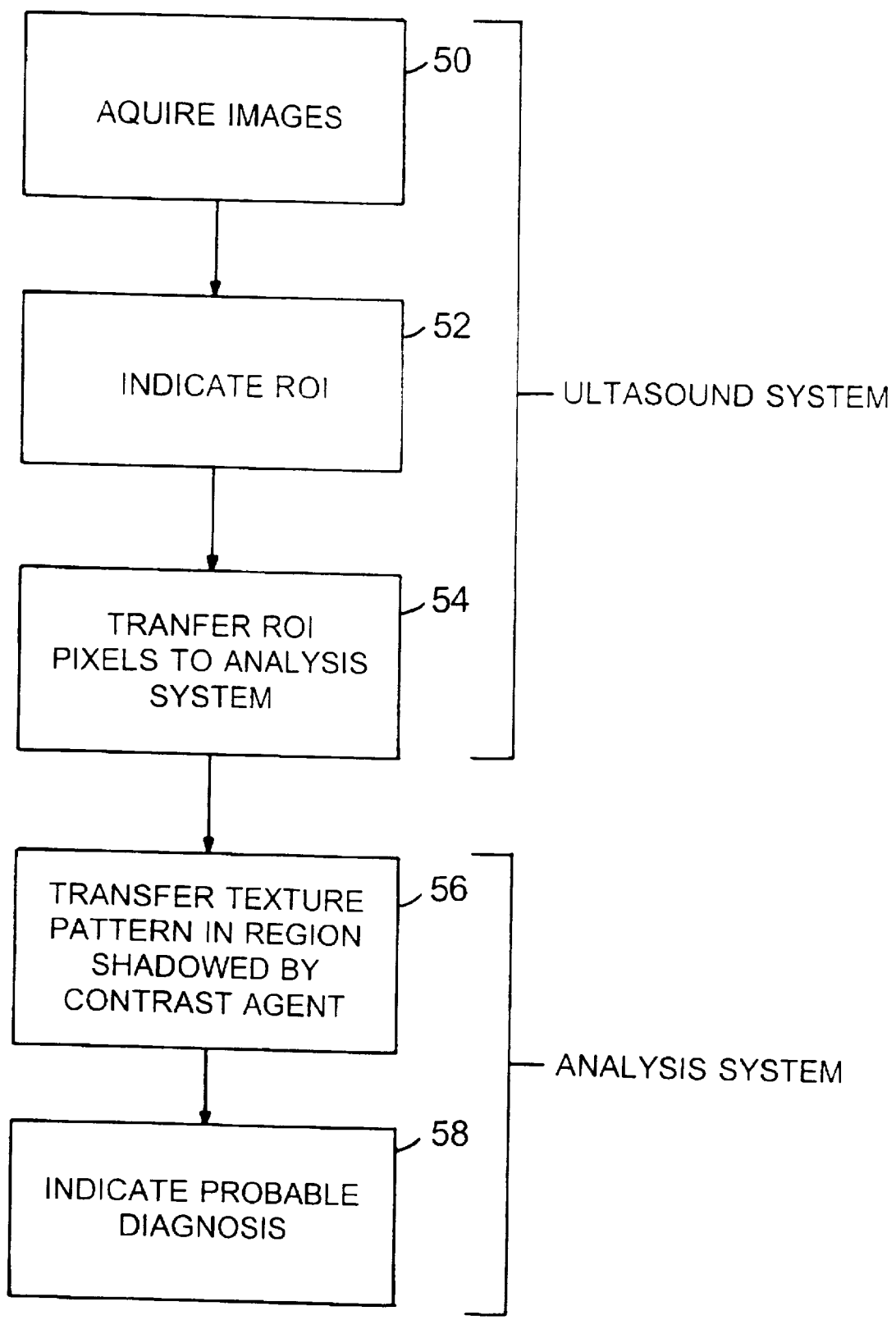
FIG. 5 is a diagram showing the process flow of the preferred embodiment of the present invention.

FIG. 5 is a diagram showing the process flow of the preferred embodiment of the present invention. Initially, images are acquired by an echocardiographic image acquisition system 30 (Step 50). In known fashion, a portion or region of interest in such images is indicated, either manually or automatically (Step 52). Digitized pixel data representing such images is then transferred to an analysis system 40 (Step 54). Such transfer may be made by direct transmission or via media transference.

The analysis system 40 is configured to analyze backscatter speckle patterns in the images that have texture characteristics that distinguish healthy from diseased tissue. Accordingly, the analysis system 40 analyzes the texture pattern of the selected myocardial regions of interest that have been shadowed by contrast agent (Step 56). A probable diagnosis (which can include a diagnosis of insufficient data) is then indicated (Step 58).

The analysis system 40 may be implemented in hardware or software, or a combination of both. However, preferably, the analysis system 40 is implemented in computer programs executing on programmable computers each comprising a processor, a data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Typical contrast agents that may be used with the invention include, but are not limited to, liquid emulsions, solids encapsulated fluids, encapsulated biocompatible gases and combinations thereof. Fluorinated liquids and gases are especially useful in contrast compositions. These types of agents include free bubbles of gas as well as those which are encapsulated by a shell material. A contrast agent may be administered via any of the known routes, including, but are not limited to, intravenous (IV), intramuscular (IM), intraarterial (IA), and intracardiac (IC).

Contrast Agent Texture Patterns

Figure 6A:
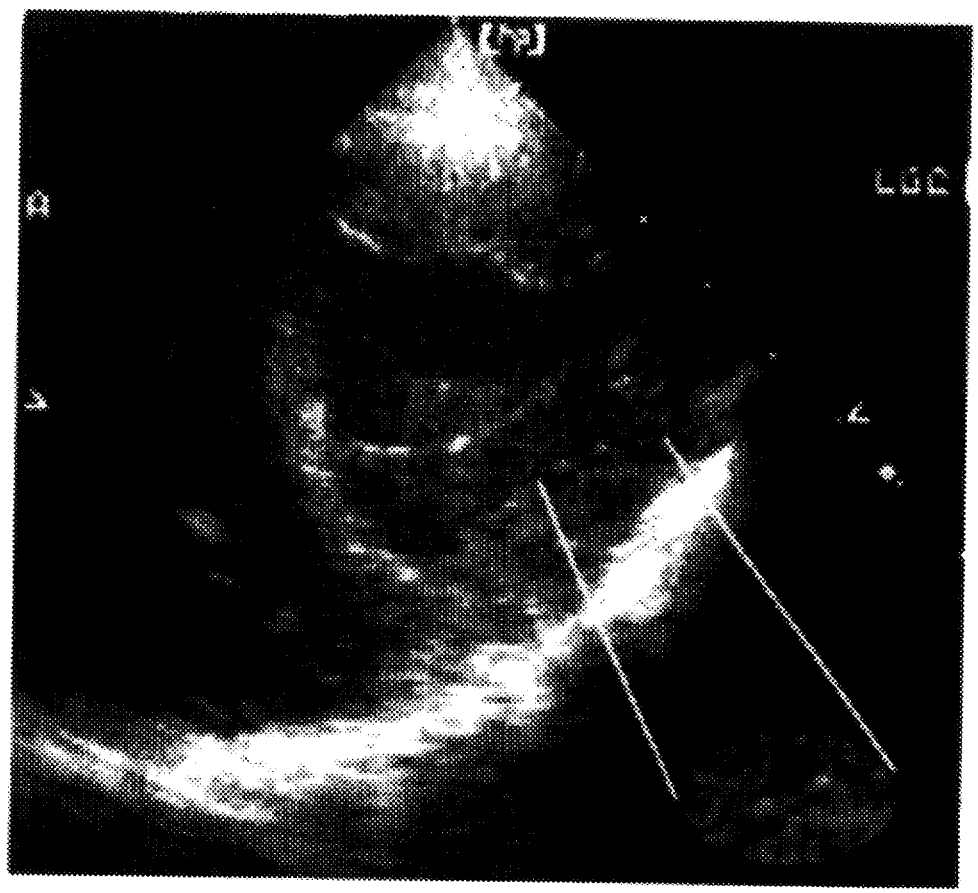
FIG. 6A is an echocardiographic image of a normal heart before contrast agent is introduced. An inset shows a magnified region of interest of normal myocardium and "texture" in the ultrasound image.

FIG. 6A is an echocardiographic image of a normal heart before contrast agent is introduced. The transducer 20 is positioned at the top of the image. An inset shows a magnified region of interest of normal myocardium and "texture" in the ultrasound image. There are bright features marking the epicardium and endocardium, caused by enhanced scattering at these tissue interfaces. Between these two structures, the appearance of the muscle (myocardium) is dark, but contains a high degree of speckling, as shown in the inset. Speckle is a well known phenomenon in ultrasound imaging and results from interference patterns from echos returning to the transducer 20 at the same time scattered off of small, closely spaced targets.

Figure 6B:
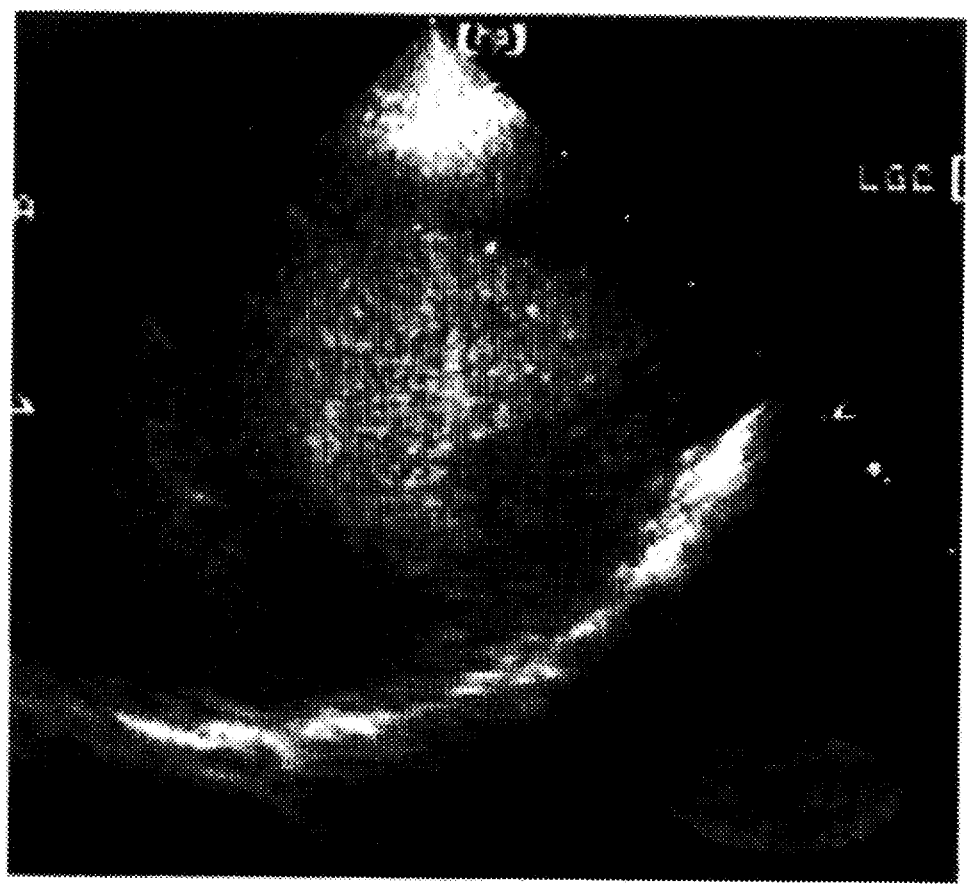
FIG. 6B is an echocardiographic image of a normal heart after contrast agent is introduced. An inset shows a magnified region of interest of contrast-perfused normal myocardium and the resultant "texture".

FIG. 6B is an echocardiographic image of a normal heart after contrast agent is introduced. Note that the central region of the organ appears very bright, due to the presence of a large amount of contrast agent in the cardiac cavity. An inset shows a magnified region of interest (corresponding to the same general region of interest as in the inset of FIG. 6A) of contrast-perfused normal myocardium and the resultant "texture". The appearance of the myocardium in the presence of contrast is different when compared to FIG. 6A. The speckle pattern differs in the presence of contrast because of the presence of a multitude of additional closely spaced, highly reflective targets (contrast agent microspheres), and because these targets are moving, as the microspheres flow with the blood. The image shown in the inset shows this difference in degree of speckle as a visually-apparent texture that is somewhat "muted" (i.e., more homogenous and lower intensity) compared to the pre-contrast image.

Figure 7A:
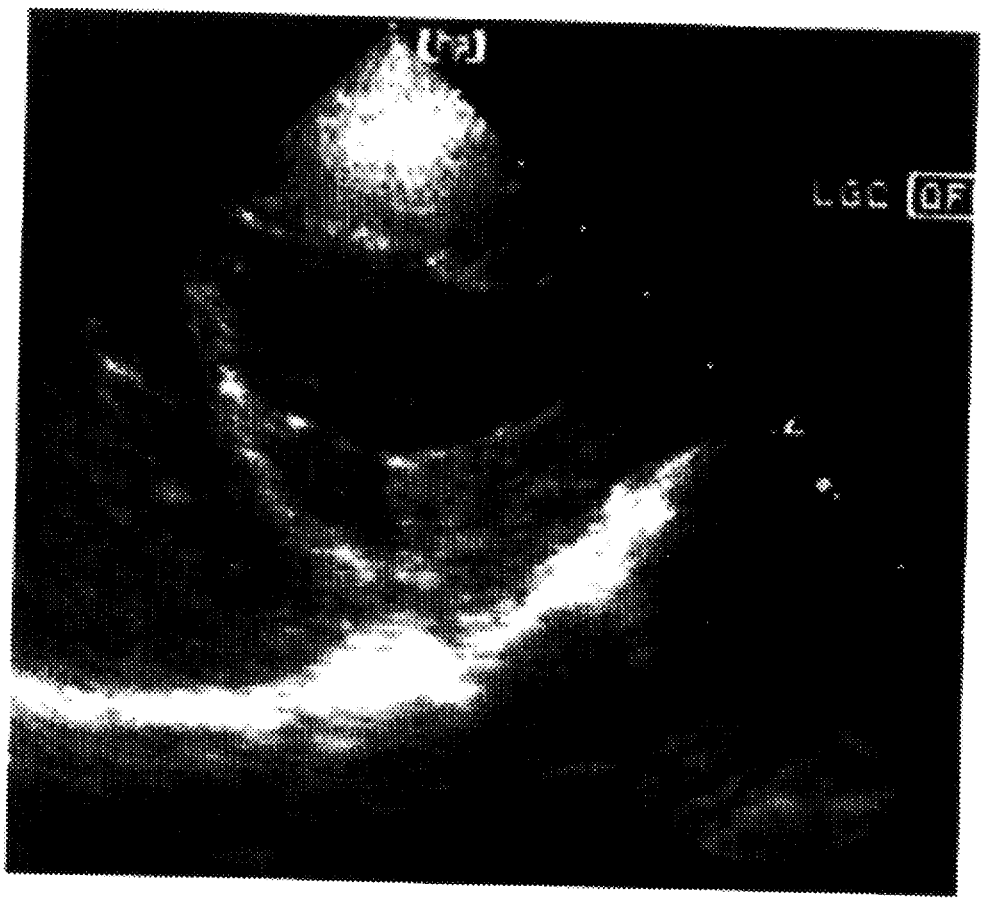
FIG. 7A is a pre-contrast agent echocardiographic image of a heart with a coronary artery occlusion, resulting in ischemia in the posterior region. An inset shows a magnified region of interest of ischemic myocardium in the absence of contrast agent.

FIG. 7A is a pre-contrast agent echocardiographic image of a heart with a coronary artery occlusion, resulting in ischemia in the posterior region. An inset shows a magnified region of interest (corresponding to the same general region of interest as in the inset of FIG. 6A) of ischemic myocardium in the absence of contrast agent. As in FIG. 6A, there are bright features marking the epicardium and endocardium, caused by enhanced scattering at these tissue interfaces. Between these two structures, the appearance of the myocardium is dark, but still contains a fair degree of speckling, as shown in the inset. However, the degree of speckling is less than in FIG. 6A because of the damaged tissue.

Figure 7B:
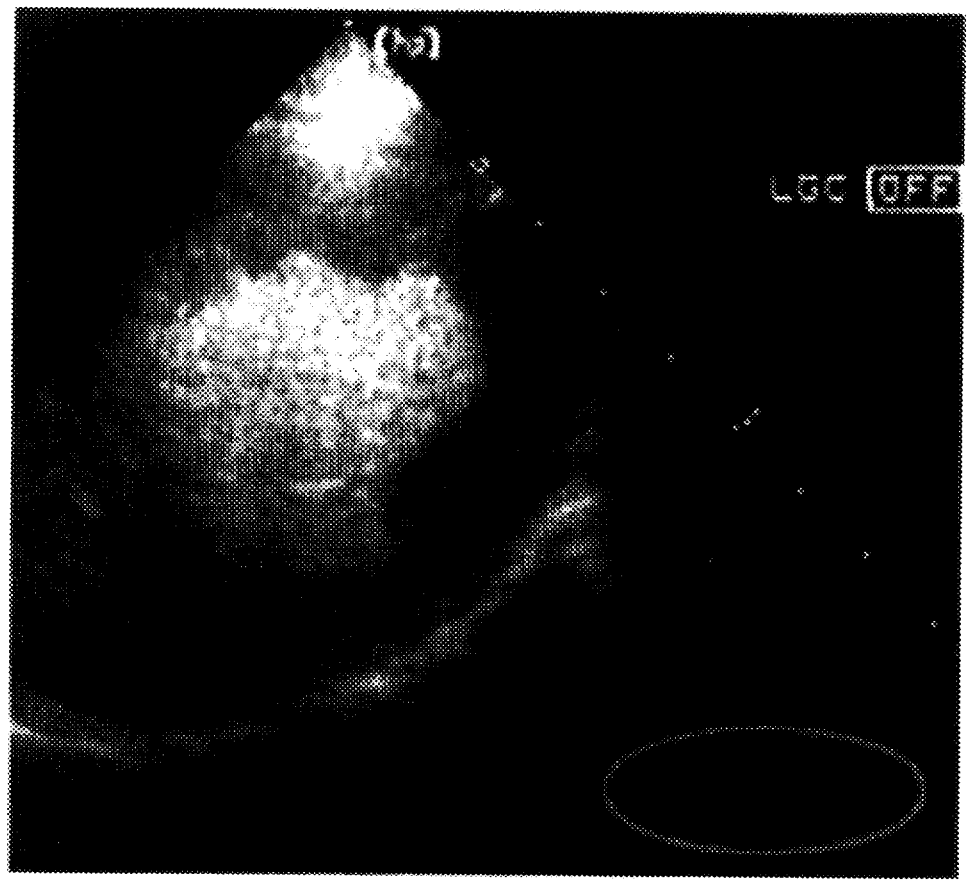
FIG. 7B is a post-contrast agent echocardiographic image of a heart with a coronary artery occlusion, resulting in ischemia in the posterior region. An inset shows a magnified region of interest of the myocardium and the resultant "texture".

FIG. 7B is a post-contrast agent echocardiographic image of a heart with a coronary artery occlusion, resulting in ischemia in the posterior region. An inset shows a magnified region of interest (corresponding to the same general region of interest as in the inset of FIG. 6A) of the myocardium and the resultant "texture". Note again that the central region of the organ appears very bright, due to the presence of a large amount of contrast agent in the cardiac cavity. The appearance of the myocardium in the presence of contrast is different when compared to FIG. 7A. The image shown in the inset shows this difference in degree of speckle as a visually-apparent texture that is quite "muted" (i.e., more homogenous and lower intensity) compared to the pre-contrast image. Note also the difference between the post-contrast image of damaged tissue in FIG. 7B compared to the pre-contrast image of healthy tissue in FIG. 6A. Note further that the post-contrast image of damaged tissue in FIG. 7B is visually distinct from the post-contrast image of healthy tissue in FIG. 6B.

Importantly, although little texture exists in FIG. 7B compared to FIG. 6B, the human eye can still discern some texture. Thus, information relating to the health of tissue in fact exists in regions of interest in ultrasound images in the presence of attenuation from interposed contrast agent, despite conventional belief to the contrary. The invention applies specialized analysis techniques, including neural network techniques, to analyze such texture patterns.

The Analysis System

FIG. 8 is a more detailed block diagram of an embodiment of the analysis system 40 used in the present invention to analyze regions of interest in ultrasound images in the presence of attenuation from interposed contrast agent, for the purpose of diagnosing abnormalities. The analysis system shown in FIG. 8 should be taken as exemplary only, since alternative analysis systems could be configured to test image data for the texture characteristics that the inventors have discovered distinguish healthy tissue from damaged tissue.

A series of echocardiographic images and electrocardiogram data comprising the input data 60 from an echocardiographic image acquisition system are coupled to a cardiac cycle phase selection module 62. The echocardiographic data is used to select from a video stream the particular images corresponding to the end-systole and end-diastole phases of each cardiac cycle, in known fashion. Only these images are passed on for further processing. The output of the cardiac cycle phase selection module 62 is coupled to several image processing modules, including a texture pyramid image module 64, a baseline-subtracted image module 66, and a signal-to-noise ratio (SNR) image module 68, which generate intermediate images. In the simplest embodiment, a user designates a region of interest (ROI) 70, using, for example, a light pen on a video monitor displaying the input data 60. The sequence of images from the image analysis modules 66–68 are clipped to the region of interest (ROI) and aggregated (e.g. by averaging within the ROI) in ROI selection and aggregation modules, and then passed to a mixture-of-experts module 74 for classification, then displayed to a user 76. A training module 78 configures the mixture-of-experts module 74 to select desired images based on known "good" (normal) and known "bad" (abnormal) images.

The sequence of selected images is applied to the texture pyramid image module 64, which applies, in the preferred embodiment, a set of oriented Gabor or wavelet filter kernels at multiple spatial scales. See, e.g., Burt, P. J.; Adelson, E. H., "The Laplacian pyramid as a compact image code", IEEE Transactions on Communications, April 1983, vol. COM-31 (no. 4):532–40. Sum-of-square energy measurements and other texture measurements can be derived from such a pyramid images by aggregation in later processing. The baseline-subtracted image module 66 generates a baseline image from unperfused images, including mean brightness and standard deviation, calculated as in the QUAMP algorithm (described below). The baseline image is then subtracted from each image in a sequence from the cardiac cycle phase selection module 62 to produce a series of baseline-subtracted images. This series of images is coupled to the SNR image module 68, which scales each image independently for each pixel by its baseline standard deviation, to produce a series of SNR images.

The mixture-of-experts module 74 preferably contains a plurality of neural networks. Neural networks can be used to identify features in images and recognize patterns and signatures in data streams. Neural networks differ from other signal processing algorithms in that they do not assume any fixed underlying model. Rather, neural networks "learn" to detect patterns by generating a model in response to input test data having known patterns, features, or other characteristics of interest in classifying the input data. Neural networks can be trained relatively easy and repeatably. Because neural networks learn to detect patterns, such neural networks are very flexible and adaptable to a wide variety of situations and conditions. This flexibility and adaptability gives neural networks a significant advantage over other data classification techniques. For further information on the architecture and training of MLP adaptive neural networks, see "Progress in Supervised Neural Networks" by Don Hush and Bill Horne, published in *IEEE Signal Processing* (January 1993).

Figure 9:
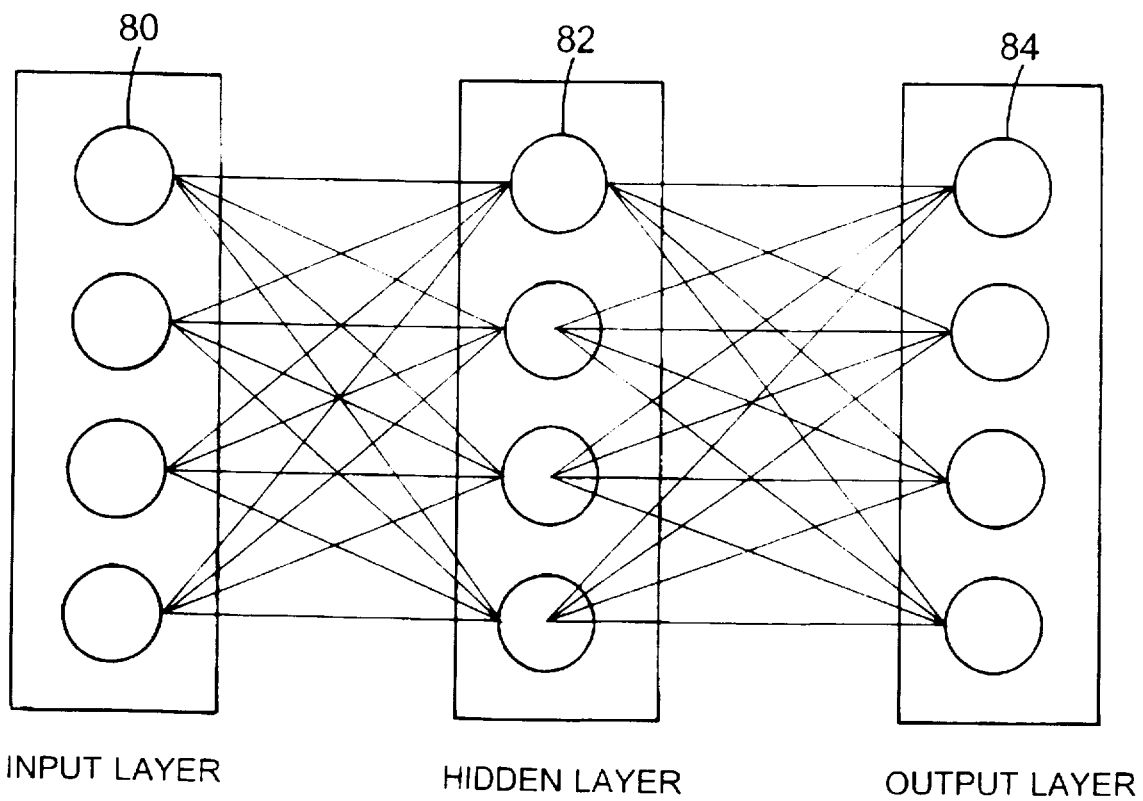
FIG. 9 is a block diagram of a standard multi-layer perceptron neural network trained by back-propagation of error.

FIG. 9 is a block diagram of one such neural network. Shown is a standard multilayer perceptron (MLP) network trained by back-propagation (BP) of error. The MLP includes input layer comprising a plurality of input units 80, a hidden layer comprising a plurality of hidden units 82, and an output layer comprising a plurality of output units 84. Each unit 82–84 is a processing element or "neuron", coupled by connections having adjustable numeric weights or connection strengths by which earlier layers influence later ones to determine the network output.

Figure 10:
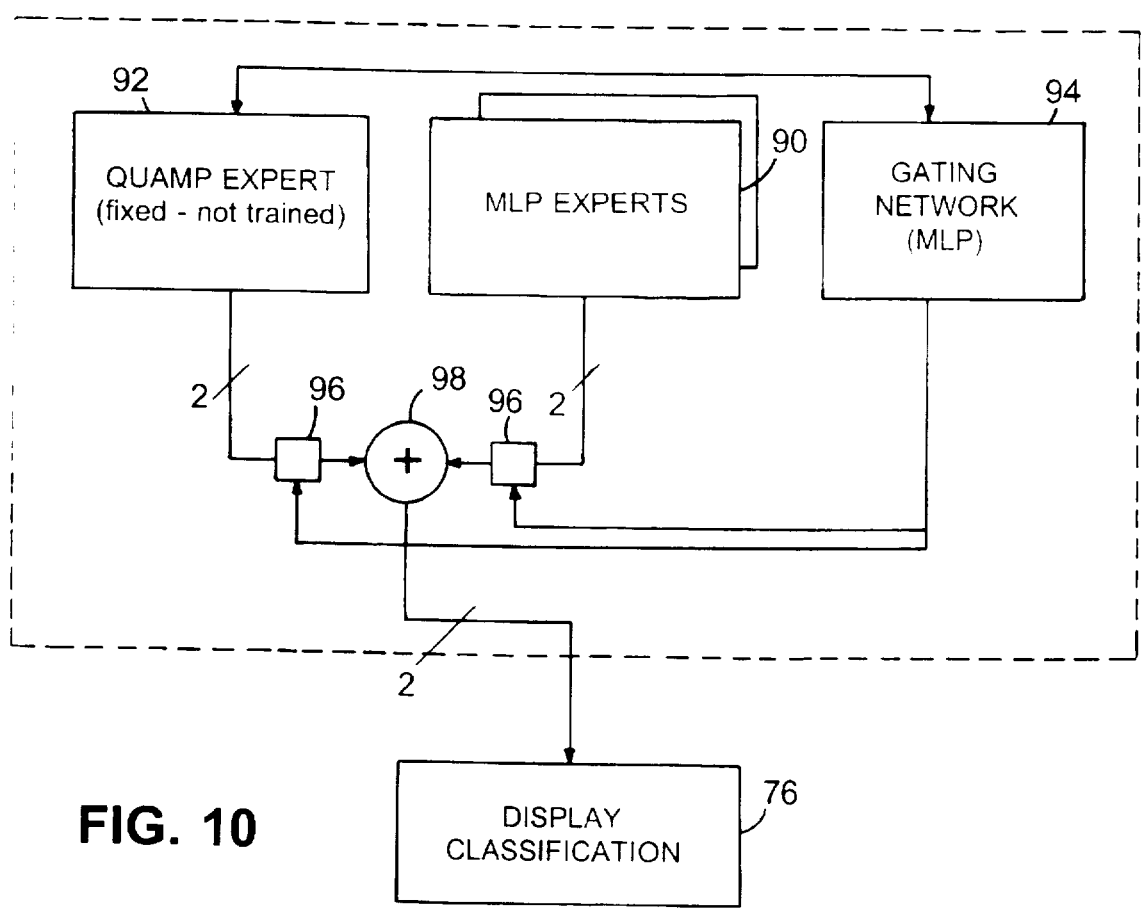
FIG. 10 is a block diagram showing the architecture of the mixture-of-experts module in greater detail.

FIG. 10 is a block diagram showing the architecture of the mixture-of-experts module 74 in greater detail. The architecture is conventional, comprising at least one adaptive neural network MLP expert module 90. Multiple expert modules 90 allow for greater subdivision of the mixture-of-experts' input pattern space into qualitatively different regions while maintaining trainability. In the preferred embodiment, the mixture-of-experts module 74 includes a nonadaptive processing expert module 92 implementing the QUAMP algorithm (described below). Each expert 90, 92 has at least two outputs which indicate whether or not the input pattern falls within corresponding categories, each representing a percentage of perfusion of contrast agent within the organ. A gating network module 94 is also implemented as an adaptive neural network MLP expert. The output of the gating network module 94 is coupled to programable "soft" multiplexors 96 and is used to modulate the outputs of each expert 90, 92. That is, after training, the gating network module 94 decides which expert 90, 92 applies to each input image, and selects that expert via a multiplexor 96. The selected output is coupled through a logical OR gate 98 to be displayed to a user 76. The output of the mixture-of-experts module 74 classifies the input data 60 into probable diagnoses. It should be understood that the selection mechanism (multiplexors 96 and OR gate 98) is itself part of the analysis system, and is configured during training of the system in conventional fashion.

Variations of the system shown in FIGS. 8–10 include:

(1) An ROI designation system 70 that tracks ROI automatically, such as by an algorithm or neural network which finds correspondences among point features (after initial selection by a user).

(2) Use of a feature-detecting image processing module to derive an image by trainable local filters (e.g., an adaptive neural network) receiving input from the other image modules 64–68. This fourth module generates an image calculated locally by an MLP feature-detecting network, which is replicated over the image and trained using back-propagation (BP) with "weight-sharing" between different copies of the network at different locations in the image.

In the preferred embodiment of the present invention, the output of the analysis system 40 indicates into which of N classes the input falls (N is an arbitrary partitioning). Thus, a diagnostician is not required to (but may) make any judgements in the analysis of the data. When used to diagnose cardiac disease, the present invention can be used accurately by most clinicians (e.g., cardiologists and general practitioners). The present invention thus may be used for screening asymptomatic patients. For example, the present invention is ideal for use in diagnosing cardiac disease before a person suffers a cardiac event such as myocardial infarction.

Figure 11:
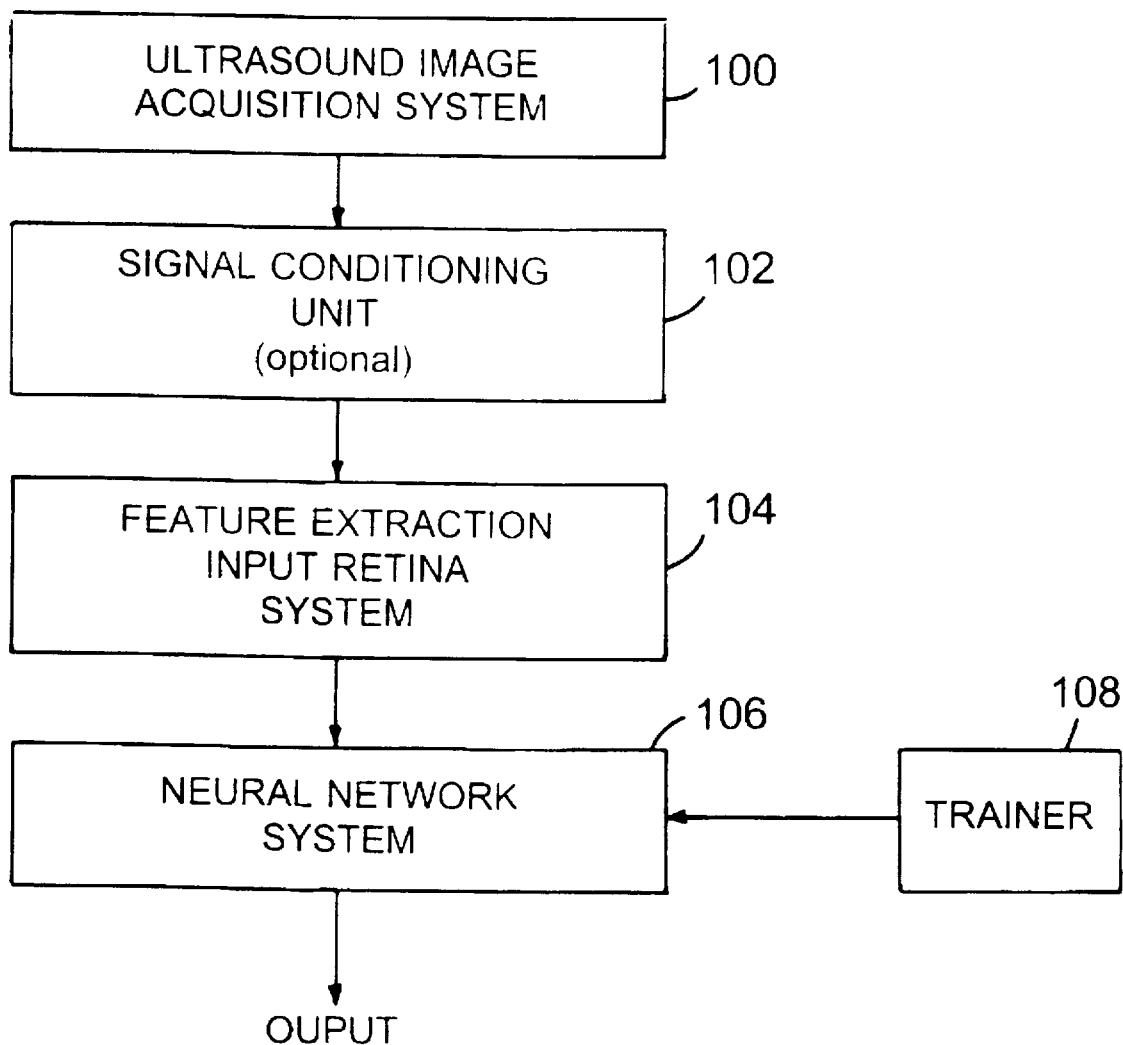
FIG. 11 is a block diagram of another way of modeling the system of FIG. 4.

FIG. 11 is a block diagram of another way of modeling the system of FIG. 4. Input images from the echocardiographic image acquisition system 100 are presented to an optional signal conditioning unit 102. The signal conditioning unit 102 provides a first level of filtering and signal processing. Signal conditioning is designed to remove signals (e.g., noise) that are not of interest to the problem at hand and to enhance those signals that are of interest. For example, the signal conditioning unit 102 may filter out 60 Hz power line hum using by applying a software digital filter to the digital input data. The signal conditioning unit 102 may also perform in software or by means of electronic circuitry such functions as automatic gain control (AGC), frequency domain smoothing, time domain adaptive/predictive filtering, and/or non-linear filtering, such as singular value decomposition, non-linear transforms, homomorphic filtering, deconvolution, and dynamic time warping. The output of the signal conditioning unit 102 is applied to a feature extraction/input retina system 104.

The feature extraction/input retina system 104 produces vectors (characteristic patterns) of features from the input data. The feature extraction/input retina system 104 performs one or more feature extraction algorithms, such as: detection of simple features, short-time fast Fourier transform, high-resolution spectra, stationary linear models, non-stationary models, non-linear transforms, vector quantization, eigenvectors/values, high-order cumulants/ bispectra/trispectra, instantaneous time/frequency distributions, cepstrum, Gabor transform, and/or wavelets. The output of the feature extraction/input retina system 104 is one or more "feature space" representations of the original input signal, each feature space representation being associated with a corresponding one of the feature extraction algorithms applied to the original input signal.

Each feature space representation of the input signal is then applied to a neural network system 106. In the illustrated embodiment, the neural network system 106 has several outputs, each of which correspond to one of the N defined classifications (e.g., percent ischemia or stenosis) For example, in the preferred embodiment of the present invention, a first category includes less than 20% coronary artery stenosis (normal), a second category includes 20–40% coronary artery stenosis, a third category includes 41–60% coronary artery stenosis, and a fourth category includes greater than 60% coronary artery stenosis. In the preferred embodiment of the present invention, an extra "insufficien data" output is reserved for situations in which the inpu contains no known signal of interest.

Prior to using the present invention to classify actual input data, a trainer 108 is used to adjust the parameters of the neural network system 106. Pre-characterized training data is applied to the neural network system 106. That is, the training data is selected such that particular known features are present. In the present invention, such data comprise time sequences (before, during, and after administration of contrast agent) of ultrasound images that include regions of interest, where the regions of interest in the various images include known normal or abnormal myocardial tissue, and where the two types of images can be distinguished by backscatter speckle texture.

The trainer 108 monitors the neural network system's output and adjusts the parameters of the neural network system 106 until the desired level of performance is achieved, in known fashion. Once an acceptable level of performance is achieved, the neural network system parameters are accepted and training stops. In the preferred embodiment of the present invention, training is done in accordance with the well-known back-propagation algorithm. This algorithm is described in an article entitled "Back-Propagation, weight elimination and time series prediction" by A. S. Weigend, D. E. Rumelhart, and B. A. Huberman, published in *Proceedings Of The 1990 Connectionist Models Summer School, pp.* 65–80 (1990), and in an article entitled "Progress in Supervised Neural Networks" by Don Hush and Bill Horne, published in *IEEE Signal Processing* (January 1993). If desired, a cross-validation system may be included, in known fashion.

Qualitative Assessment of Myocardial Perfusion—QUAMP

The following describes a non-trained algorithm that provides a measure of myocardial perfusion found useful in predicting the existence of "texture" in echocardiograms taken in the presence of contrast agent. The description is of an actual experiment. This algorithm is implemented in the present embodiment by means of the cardiac cycle phase selection module 62, the baseline-subtracted image module 66, the signal-to-noise ratio (SNR) image module 68, and the nonadaptive processing expert module 92.

Copies of echocardiogram images were made from original videotapes; although this introduces some noise, this allows the closest comparison to the quality of the images viewed by the echocardiographers. While the copied video tape was played on a video cassette recorder, the images were transferred to a laser videodisc recorder. Images at the same point in the cardiac cycle were then manually chosen, based on an ECG trace recorded on the videotape, for transfer from the videodisc recorder to a computer via a frame capture board. The images were digitized with a spatial resolution of 660×485 pixels per frame and a brightness resolution of 8 bits (256 grey levels). Myocardial perfusion assessments were made separately from images at end systole and end diastole.

A rectangular region of interest (ROI) was demarcated for each myocardial segment within a sequence of images from a patient. The region of interest was located to include tissue from the subepicardium to the subendocardium. For seven patients, two different ultrasound scanners were used, which had slightly different image formats. In addition, for the different patients, images were formed from different depths of ultrasonic penetration, either 10 cm or 12 cm. These factors, together with the fact that the six myocardial segments with a single view or between views were different sizes, meant that the sizes of the ROI varied from patient to patient and segment to segment. Any correction for motion between frames was made manually, i.e., the operator adjusted the placement of the region of interest for each frame as necessary.

The analysis method used was designed to require less operator intervention and be more independent of the scanner gain settings. For these reasons, the analysis used the following algorithm:

Frames in which contrast does not visually appear were designated as baseline frames.

Video intensity vs. time was evaluated for each pixel within the ROI.

For image sequences that contained 10 or more baseline frames, a simple non-weighted, linear regression was performed on the pixel intensity vs. time plot for the baseline frames. In addition to the slope and intercept, the rms error of the fit, $\sigma_{base}$, was determined. From this fit, the baseline pixel intensity was estimated for frames during which contrast appeared. If the estimated baseline pixel intensity was negative, resulting from a negative slope, then the baseline pixel intensity was taken to be zero.

For image sequences containing fewer than 10 baseline frames, the mean of the pixel intensity over the baseline frames was calculated. The estimated baseline pixel intensity for frames during which contrast appeared was taken as the mean.

The noise in the baseline, $\sigma_{base}$, was taken as the standard deviation of the pixel intensity over the baseline frames.

For each frame, the estimated baseline pixel intensity was subtracted from the observed pixel intensity, so that the signal solely from contrast, $S_i$, is determined. In instances where attenuation caused shadowing in the image, the observed pixel intensity may have decreased to an extent to be less than the estimated baseline intensity. In such instances, $S_i$, was taken to be zero.

For the image with the maximum signal above the noise, $S_k$, a composite signal to noise ratio was determined from the signal, $S_k$, and the signal from the following cardiac cycle, $S_{k+1}$. A peak signal may arise from spurious noise, so the signals were weighted as follows:

$$(S/N)_k = \frac{0.1 S_k + 0.9 S_{k+1}}{\sigma_{base}} \qquad \text{Eqn. (1)}$$

The signal-to-noise ratio was treated as a standardized, normal variable and the probability density of obtaining the observed S/N from random noise fluctuations was calculated as follows:

$$P(S/N)_k = \frac{1}{\sqrt{2\pi}} e^{-\frac{(S/N)_k^2}{2}} \qquad \text{Eqn. (2)}$$

A pixel that had a large increase in the video intensity over the course of the injection of contrast agent compared to the baseline noise will have a large signal-to-noise ratio and a small probability of that signal-to-noise ratio deriving from noise alone.

Using this algorithm, a receiver operating curve (ROC) analysis determined the thresholds for perfusion by maximizing the area under the ROC curve. A pixel was considered to have brightened if the probability density was less than 0.28, corresponding to $S/N \geq 0.84$. A region was considered to have been perfused if 40% of the pixels in the region had brightened. At these thresholds, the area under the ROC curve was 0.84. (An area of 0.5 indicates that a procedure agrees in a random fashion with the "gold standard" of perceptible radio-labeled microspheres, while an area of 1.0 corresponds to perfect agreement with the "gold standard".) The operating point along the ROC curve was chosen to be where the slope of the line tangent to the curve is 1, a point that shows no bias toward sensitivity or specificity. At this operating point, the sensitivity is 79%, the specificity is 72%, the positive predictive value is 66%, and the negative predictive value is 69%.

Assessments were made at end systole and diastole. For comparison to the ratings of a panel of echocardiographers, the ratings at end systole and end diastole were combined (and referred to simply as "QUAMP"), so that if perfusion was observed at either point in the cardiac cycle, it was considered as perfused.

While the QUAMP algorithm described above is one expert system that may be applied in the mixture-of-experts module 74, other algorithms may be used as well that provide measurements of texture. Such algorithms may, for example, measure texture in the presence of contrast agent using such techniques as the Gabor transform; fractal dimension (Veenland, et al., *Med. Phys.*, 23 585 (1996)); moments of the histogram distribution (e.g., standard deviation, skewness, kurtosis); spatial gray level dependence matrix (co-occurrence matrix) (Chan, et al., *Phys. Med. Bio.*, 40 857 (1995)) for factors such as correlation, entropy, energy (angular second moment), inertia, inverse different moment, sum average, sum entropy, difference entropy; autocorrelation; gray level run lengths (Skorton, et al., *Circulation*, 66 217 (1993)); parameters of the distribution (Goldberg, et al., *Trans. Med. Imag.*, 12 687 (1993)); and/or characteristic function ("Guide to Standard Mathematica® Packages", version 2.2, Adamchik et. al. (Wolfram Research, Champaign, Ill. 1993). In addition to texture characteristics, any other information obtained from an echocardiogram may be analyzed for use as an expert system (e.g., wall thickening and wall motion).

Summary

In summary, the preferred embodiment of the present invention includes: (1) a data acquisition system for acquiring ultrasound image data indicative of a region of interest in the presence of attenuation from interposed contrast agent; (2) an optional signal conditioning stage to remove signals (e.g., noise) from the input data; and (3) an analysis system designed to detect "texture" characteristics that distinguish healthy tissue from diseased tissue even in the presence of the contrast agent. Since the invention can be implemented using relatively inexpensive equipment, the invention provides an inexpensive method and apparatus for accurately and consistently analyzing complex input data representing varied anatomical conditions in which the characteristics are very complex, enigmatic, or are hidden among or overwhelmed by competing noise and other signals which obscure the characteristics of interest.

A number of embodiments of the present invention have been described. Nevertheless, it will be understood that various modifications may be made without departing from the spirit and scope of the invention. For example, the present invention can be applied to characterizing two-dimensional image data derived from X-rays, MRI devices, CT, PET, and other image-generating techniques where regions of interest are obscured by the presence of a contrast agent until the contrast agent clears sufficiently from the organ. Further, the imaging sonification frequency may be alternated between relatively high frequency (e.g., more than 10 fps) and relatively low frequency (e.g., less than or equal to about 10 fps) in order to provide "real-time" views versus intermittent but higher "contrast" (due to better signal-to-noise ratio) views. As another example, the region of interest may be selected before generation of intermediate images. Accordingly, it is to be understood that the invention is not to be limited by the specific illustrated embodiment, but only by the scope of the appended claims.

What is claimed is:

1. A method of characterizing a region of interest in a plurality of images of a contrast-enhanced organ, comprising the steps of:

(a) generating a set of digitized images of the region of interest;

(b) analyzing the set of digitized images of the region of interest by means of an analysis system configured to recognize contrast agent texture patterns in such digitized images indicative of tissue health in the organ;

(c) indicating, based on such analysis, if the region of interest is probably normal or abnormal.

2. The method of claim 1, wherein the images are ultrasound images.

3. The method of claims 1 or 2, wherein the images are generated by a B-mode ultrasound system.

4. The method of claims 1 or 2, wherein the images are generated by a Doppler ultrasound system.

5. The method of claims 1 or 2, wherein the images are generated by a harmonic ultrasound system.

6. The method of claims 1 or 2, wherein the images are generated by a three-dimensional ultrasound system.

7. The method of claims 1 or 2, wherein the organ is a heart.

8. The method of claim 7, wherein the images are taken at approximately the same point in the cardiac cycle of the heart.

9. The method of claims 1 or 2, wherein the organ is a kidney.

10. The method of claims 1 or 2, wherein the organ is a brain.

11. The method of claims 1 or 2, wherein the organ is a liver.

12. The method of claims 1 or 2, wherein the organ is a testis.

13. The method of claims 1 or 2, wherein the organ is a muscle.

14. The method of claim 1, wherein the indication of normal or abnormal pertains to degree of blood flow within the organ.

15. The method of claim 1, wherein the step of analyzing the set of images comprises the further steps of:

(a) generating a plurality of filtered intermediate images from each image;

(b) applying a set of expert analysis modules to the intermediate images to classify the set of images as probably normal or abnormal.

16. The method of claim 1, wherein the contrast agent is chosen from the group consisting of liquid emulsions, solids, encapsulated fluids, encapsulated biocompatible gases, and combinations thereof.

17. The method of claim 16, wherein the contrast agent employs a fluorinated gas or liquid.

18. The method of claim 1, wherein the images are x-ray images.

19. The method of claim 1, wherein the images are MR images.

20. The method of claim 1, wherein the images are CT images.

21. The method of claim 1, wherein the images are PET images.

22. The method of claim 1, wherein the images are SPECT images.

23. A system for characterizing a region of interest in a plurality of images of a contrast-enhanced organ, comprising:

(a) means for generating a set of digitized images of the region of interest;

(b) means for analyzing the set of digitized images of the region of interest by means of an analysis system configured to recognize contrast agent texture patterns in such digitized images indicative of tissue health in the organ;

(c) means for indicating, based on such analysis, if the region of interest is probably normal or abnormal.

24. The system of claim 23, wherein the images are ultrasound images.

25. The system of claims 23 or 24, wherein the images are generated by a B-mode ultrasound system.

26. The system of claims 23 or 24, wherein the images are generated by a Doppler ultrasound system.

27. The system of claims 23 or 24, wherein the images are generated by a harmonic ultrasound system.

28. The system of claims 23 or 24, wherein the images are generated by a three-dimensional ultrasound system.

29. The system of claims 23 or 24, wherein the organ is a heart.

30. The system of claim 29, wherein the images are taken at approximately the same point in the cardiac cycle of the heart.

31. The system of claims 23 or 24, wherein the organ is a kidney.

32. The system of claims 23 or 24, wherein the organ is a brain.

33. The system of claims 23 or 24, wherein the organ is a liver.

34. The system of claims 23 or 24, wherein the organ is a testis.

35. The system of claims 23 or 24, wherein the organ is a muscle.

36. The system of claim 23, wherein the indication of normal or abnormal pertains to degree of blood flow within the organ.

37. The system of claim 23, wherein the means for analyzing the set of images further comprises:

(a) means for generating a plurality of filtered intermediate images from each image;

(b) means for applying a set of expert analysis modules to the intermediate images to classify the set of images as probably normal or abnormal.

38. The system of claim 23, wherein the contrast agent is chosen from the group consisting of liquid emulsions, solids, encapsulated fluids, encapsulated biocompatible gases, and combinations thereof.

39. The system of claim 38, wherein the contrast agent employs a fluorinated gas or liquid.

40. The system of claim 23, wherein the images are x-ray images.

41. The system of claim 23, wherein the images are MRI images.

42. The system of claim 23, wherein the images are CT images.

43. The system of claim 23, wherein the images are PET images.

44. The system of claim 23, wherein the images are SPECT images.

45. A computer program, residing on a computer-readable medium, for characterizing a region of interest in a plurality of images of a contrast-enhanced organ, the computer program comprising instructions for causing a processor to:

(a) receive a set of digitized images of the region of interest;

(b) analyze the set of digitized images of the region of interest by means of an analysis system configured to recognize contrast agent texture patterns in such digitized images indicative of tissue health in the organ;

(c) indicate, based on such analysis, if the region of interest is probably normal or abnormal.

46. The computer program of claim 45, wherein the images are ultrasound images.

47. The computer program of claims 45 or 46, wherein the images are generated by a B-mode ultrasound system.

48. The computer program of claims 45 or 46, wherein the images are generated by a Doppler ultrasound system.

49. The computer program of claims 45 or 46, wherein the images are generated by a harmonic ultrasound system.

50. The computer program of claims 45 or 46, wherein the images are generated by a three-dimensional ultrasound system.

51. The computer program of claims 45 or 46, wherein the organ is a heart.

52. The computer program of claim 51, wherein the images are taken at approximately the same point in the cardiac cycle of the heart.

53. The computer program of claims 45 or 46, wherein the organ is a kidney.

54. The computer program of claims 45 or 46, wherein the organ is a brain.

55. The computer program of claims 45 or 46, wherein the organ is a liver.

56. The computer program of claims 45 or 46, wherein the organ is a testis.

57. The computer program of claims 45 or 46, wherein the organ is a muscle.

58. The computer program of claim 45, wherein the indication of normal or abnormal pertains to degree of blood flow within the organ.

59. The computer program of claim 45, wherein the computer program further comprises instructions for causing the processor to:

(a) generate plurality of filtered intermediate images from each image;

(b) apply a set of expert analysis modules to the intermediate images to classify the set of images as probably normal or abnormal.

60. The computer program of claim 45, wherein the contrast agent is chosen from the group consisting of liquid emulsions, solids, encapsulated fluids, encapsulated biocompatible gases, and combinations thereof.

61. The computer program of claim 60, wherein the contrast agent employs a fluorinated gas or liquid.

62. The computer program of claim 45, wherein the images are x-ray images.

63. The computer program of claim 45, wherein the images are MRI images.

64. The computer program of claim 45, wherein the images are CT images.

65. The computer program of claim 45, wherein the images are PET images.

66. The computer program of claim 45, wherein the images are SPECT images.

* * * * *